(12) United States Patent
Byager

(10) Patent No.: US 10,194,938 B2
(45) Date of Patent: Feb. 5, 2019

(54) INSERTER SYSTEM WITH TRANSPORT PROTECTION

(75) Inventor: Rune Frimand Byager, Frederiksberg (DK)

(73) Assignee: UnoMedical, AS (DK)

( * ) Notice: Subject to any disclaimer, the term of this patent is extended or adjusted under 35 U.S.C. 154(b) by 395 days.

(21) Appl. No.: 14/003,193

(22) PCT Filed: Mar. 5, 2012

(86) PCT No.: PCT/EP2012/053722
§ 371 (c)(1),
(2), (4) Date: Nov. 12, 2013

(87) PCT Pub. No.: WO2012/123274
PCT Pub. Date: Sep. 20, 2012

(65) Prior Publication Data
US 2015/0157361 A1 Jun. 11, 2015

Related U.S. Application Data

(60) Provisional application No. 61/452,836, filed on Mar. 15, 2011.

(30) Foreign Application Priority Data

Mar. 14, 2011 (EP) ..................................... 11158118

(51) Int. Cl.
*A61B 17/34* (2006.01)
*A61M 5/158* (2006.01)
(Continued)

(52) U.S. Cl.
CPC .......... *A61B 17/3468* (2013.01); *A61B 5/686* (2013.01); *A61B 17/3415* (2013.01);
(Continued)

(58) Field of Classification Search
CPC .............. A61B 5/1411; A61B 17/3415; A61B 17/3468; A61M 5/158; A61M 2005/1585
See application file for complete search history.

(56) References Cited

U.S. PATENT DOCUMENTS

2004/0127818 A1* 7/2004 Roe .................. A61B 5/150022
600/583
2005/0101912 A1 5/2005 Faust
(Continued)

FOREIGN PATENT DOCUMENTS

WO WO 2009/010399 1/2009
WO WO 2012/123274 9/2012

OTHER PUBLICATIONS

PCT/EP2012/053722 International Preliminary Report on Patentability dated Sep. 17, 2013.
(Continued)

*Primary Examiner* — Thomas McEvoy
(74) *Attorney, Agent, or Firm* — Wilson Sonsini Goodrich & Rosati

(57) ABSTRACT

Single use inserter system comprising a housing part and a lid part, the inserter system comprising a carrier part in an initial position in the housing and a drive unit comprising a first drive part attached to the housing, the drive unit comprising at least one spring element supported by the first drive part, wherein the drive unit is configured for moving the carrier part from a first position to a second position in relation to the housing in an insertion direction along a first axis. The inserter system comprises a transcutaneous device having a proximal surface and a distal surface, wherein the transcutaneous device is detachably attached to the carrier part, the inserter system comprising at least one transport protection element preventing movement of the carrier part
(Continued)

in a direction along the first axis thereby supporting the carrier part in the initial position.

13 Claims, 7 Drawing Sheets

(51) Int. Cl.
*A61B 5/00* (2006.01)
*A61B 17/00* (2006.01)
(52) U.S. Cl.
CPC ..... *A61M 5/158* (2013.01); *A61B 2017/0023* (2013.01); *A61B 2017/00367* (2013.01); *A61B 2017/347* (2013.01); *A61M 2005/1585* (2013.01)

(56) References Cited

U.S. PATENT DOCUMENTS

| 2007/0021729 A1* | 1/2007 | Mogensen ............ A61M 5/002 604/500 |
| 2009/0218243 A1* | 9/2009 | Gyrn et al. .................. 206/365 |
| 2011/0028982 A1 | 2/2011 | Lacy |

OTHER PUBLICATIONS

PCT/EP2012/053722 Written Opinion completed Mar. 29, 2012.
PCT/EP2012/053722 International Search Report completed Mar. 29, 2012.

* cited by examiner

INSERTER SYSTEM WITH TRANSPORT PROTECTION

This application claims the benefit under 35 U.S.C. § 371 of International Application No. PCT/EP2012/053722, filed Mar. 5, 2012, which claims the benefit of European Application No. 11158118.7, filed Mar. 14, 2011 and U.S. Provisional Application Ser. No. 61/452,836, filed Mar. 15, 2011, which are incorporated by reference herein in their entirety.

The present invention relates to an inserter system, in particular a single use inserter system for placing a transcutaneous device on or near the skin of a patient.

Inserter devices that require manual loading of a drive prior to insertion through the skin of a patient typically have a carrier part carrying the transcutaneous device, wherein the carrier part is in an initial position prior to use, i.e. during storage and transportation, wherein the drive is unbiased/unloaded or substantially unbiased. During transportation, the inserter device may be subject to shock or bumps, which may lead to movement of the unbiased carrier part possibly causing breakage of the packaging, e.g. separation of a seal or cover sheet from the housing. Further, shocks or bumps affecting the inserter system may result in displacement of the transcutaneous device in relation to the carrier part. Displacement of the transcutaneous device may lead to discomfort during insertion or even malfunction of the inserter system.

Typically, preloading of inserter devices with spring elements made of a plastic material, such as POM, is not suitable due to the material properties of the spring element material. Accordingly for inserter devices with plastic spring elements, the drive unit is typically unloaded or substantially unloaded in the initial or transport position, thus requiring loading of a drive unit of the inserter device prior to placing or inserting a transcutaneous part of the inserter device.

SUMMARY

There is a need for inserter systems with capability of withstanding shocks and bumps, e.g. during transportation or relocation.

Accordingly, an inserter system is provided, the inserter system being a single use inserter system comprising a housing part and a lid part, the inserter system comprising a carrier part in an initial position in the housing and a drive unit comprising a first drive part attached to the housing, the drive unit comprising at least one spring element supported by the first drive part, wherein the drive unit is configured for moving the carrier part from a first position to a second position in relation to the housing in an insertion direction along a first axis. The inserter system may comprise a transcutaneous device having a proximal surface and a distal surface, wherein the transcutaneous device is detachably attached to the carrier part, and the inserter system may comprise at least one transport protection element preventing movement of the carrier part in a direction along the first axis thereby supporting the carrier part in the initial position.

The inserter system provides an improved inserter system with increased strength and which is able to withstand shocks and bumps typically experienced during transport and storage without damaging the inserter system.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

The figures are schematic and simplified for clarity, and they merely show details which are essential to the understanding of the invention, while other details have been left out. Throughout, the same reference numerals are used for identical or corresponding parts.

DETAILED DESCRIPTION

Figure 1:
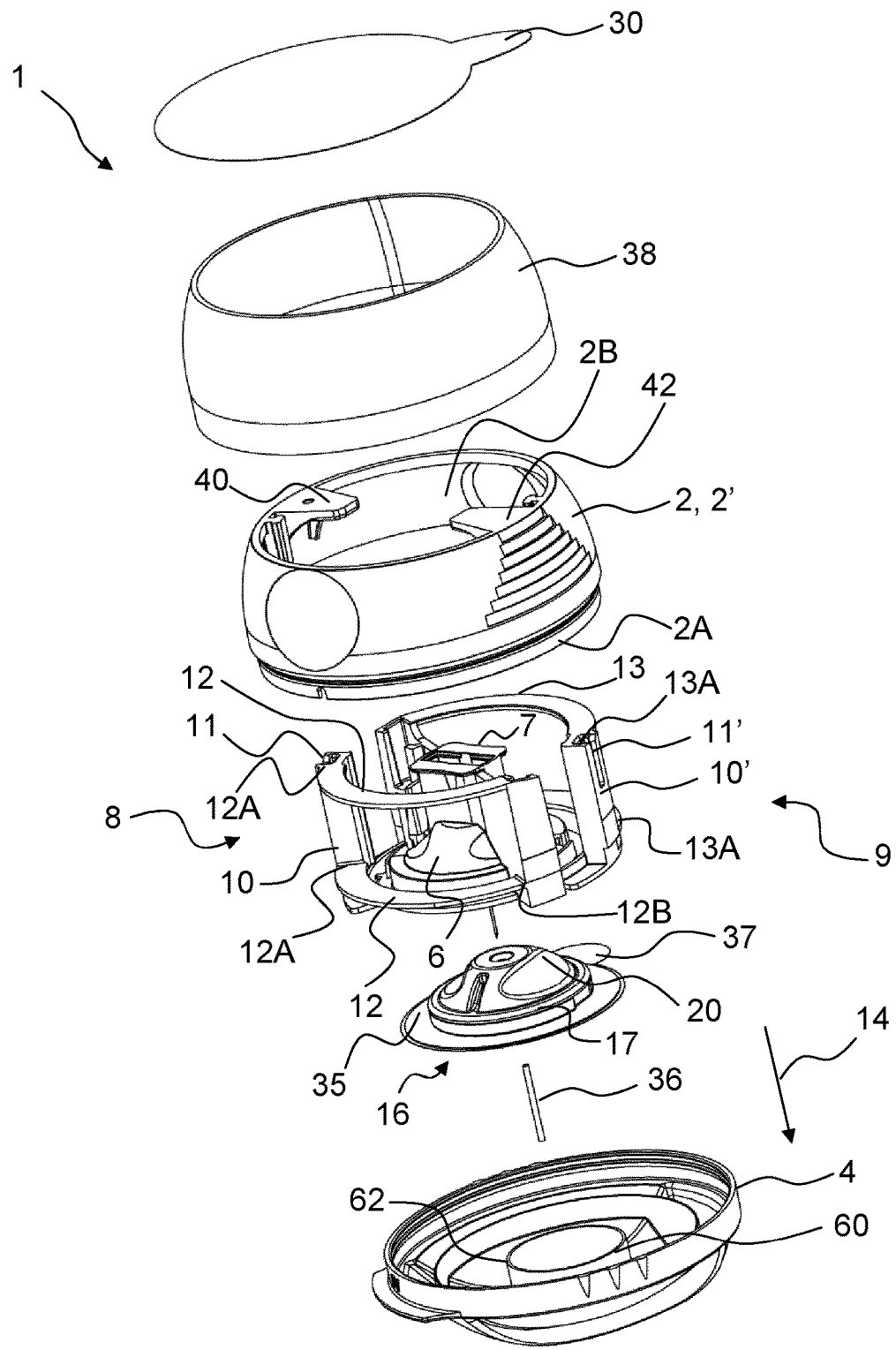
FIG. 1 is an exploded view of an exemplary inserter system.

The inserter system of the present invention alleviates the problems experienced with inserter devices with unbiased drive units.

The inserter system comprises a housing part and optionally a lid part. The housing part has a sidewall with a first end and a second end. A first opening and/or a second opening may be provided at the first end and second end, respectively. When assembled, the lid part may cover the first opening at the first end.

The inserter system may comprise a gas permeable seal or cover sheet. The seal may cover the second opening at the second end of the housing part. The housing part, the seal, and optionally the lid part may define a closed cavity accommodating the transcutaneous device in a sterile environment prior to use. The gas permeable seal allows sterilization of the inserter system upon assembly.

The inserter system comprises a transcutaneous device comprising a base with a distal surface and a proximal surface, the transcutaneous device comprising a transcutaneous element, such as a cannula and/or a sensor element, mounted to the base extending from the proximal surface facing the skin of a patient. The proximal surface may be an adhesive surface for securing the transcutaneous device to a base plate and/or on the skin of the patient. A mounting pad with an adhesive surface may be attached to the proximal surface of the base of the transcutaneous device. The inserter system may comprise a protective layer covering the adhesive surface. The transcutaneous device may comprise locking elements for locking engagement with a base plate.

Prior to use, the carrier part is in an initial position. Prior to inserting the transcutaneous device, a user has to load the inserter system. During loading of the inserter system, the carrier part and the transcutaneous device are moved by the user from the initial position to a first position also referred to as a loaded position or retracted position, e.g. in a retraction direction opposite the insertion direction. By moving the carrier part, e.g. along the first axis and/or around the first axis, to the first position, the drive unit connected to or supporting on the carrier part is biased or loaded for moving the carrier part and the transcutaneous device from the first position to a second position also referred to as an injection position. In the first position, the carrier part is releasably locked by one or more first locking elements, such as a first primary locking element and/or a first secondary locking element on the carrier part. In the first position, the first locking elements may support on a stationary part of the inserter system including the housing part and/or the first drive part. After loading, the inserter system is positioned on the skin and the carrier part is released. Upon release of the first locking element(s), the loaded drive unit moves the carrier part and the transcutaneous device in the insertion direction to the second position placing the transcutaneous element under the skin. After insertion, the carrier part and housing part are removed and the transcutaneous element, optionally including tubing, is ready for use.

The carrier part of the inserter system may comprise a needle hub with a hub base and optionally an insertion needle secured to the hub base, wherein the transcutaneous device is detachably attached to the needle hub. The carrier part may comprise a carrier base, wherein the needle hub is releasably attached to the carrier base. The inserter device may be configured for releasing the needle hub from the carrier base, e.g. in the second position. The inserter device may be configured for moving the needle hub to a third position in the extraction direction upon release from the carrier base in the second position.

The carrier part, with or without an insertion needle, and the drive unit may be molded in a single first unit reducing assembly costs.

The inserter system comprises a stationary part. The stationary part is the parts of the inserter system that are stationary in relation to the skin of a patient when the transcutaneous device is inserted. The stationary part comprises the housing part and at least the first drive part(s).

The at least one transport protection element provides a releasable support or locking of the carrier part and/or transcutaneous device in the initial position, thereby preventing or limiting movement of the carrier part and/or transcutaneous device in the insertion direction and/or in the extraction direction opposite the insertion direction along the first axis. Thus, the transport protection elements may provide that the transcutaneous device in the initial position is substantially fixed or secured in relation to the carrier part thereby avoiding user discomfort or malfunction of the inserter system during use. Further, the transport protection element(s) may provide fixation of the carrier part and/or the transcutaneous device in relation to the stationary part reducing or eliminating the risk of breaking the seal or cover sheet during transportation.

The at least one transport protection element may comprise at least one bridge between the carrier part and the stationary part of the inserter system. The at least one bridge has dimensions or weakened sections that enable a user to break the bridges when loading the inserter system in order to move the carrier part to the first position in relation to the stationary part. At the same time, the bridge dimensions are selected to withstand forces resulting from transport bumps or shocks, thereby securing the carrier part in the initial position.

A bridge may comprise one or more weakened sections. A weakened section may have a minimum width in the range from about 0.1 mm to about 2.0 mm, such as in the range from 0.3 mm to 1.5 mm, e.g. about 1.0 mm. A weakened section may have a minimum thickness in the range from about 0.1 mm to about 2.0 mm, such as in the range from 0.3 mm to 1.5 mm, e.g. about 0.5 mm. A weakened section of a bridge may have a minimum cross sectional area in the range from 0.1 mm$^2$ to about 4.0 mm$^2$, such as in the range from about 0.3 mm$^2$ to about 2.0 mm$^2$, e.g. 0.5 mm$^2$, 0.8 mm$^2$ or 1.0 mm$^2$ The first unit may be made of a suitable polymer material such as polyoxymethylene (POM).

The at least one transport protection element may comprise a locking member detachably mounted in the housing. The locking member may engage with or supporting on the carrier part and/or a stationary part of the inserter system, such that movement of the carrier part in a direction, e.g. the insertion direction and/or the extraction direction, along the first axis in relation to the stationary part is limited or substantially prevented, thereby supporting the carrier part in the initial position. The locking member may limit or substantially prevent movement of the transcutaneous device in the extraction direction and/or in the insertion direction.

The at least one transport protection element may comprise at least one support element formed in the lid part. The at least one support element may include a first support element for supporting the carrier part and the transcutaneous device in the initial position. The first support element may have a first end positioned adjacent to the proximal surface of the transcutaneous device limiting or substantially preventing movement of the transcutaneous device in the insertion direction.

A first support element may be formed as a cylindrical tube having a first end and a suitable cross section, such as circular with a first diameter $d_1$, rectangular, oval, or any other suitable shape. The first support element may extend perpendicular to the first axis. The first support element may be arranged to support the transcutaneous device in the initial position by the first end of the first support element forming a stop member in the insertion direction. The distance between the first end of the first support element and the proximal surface of the transcutaneous device should be small enough to prevent displacement of the transcutaneous device in relation to the carrier part and/or the stationary part in the insertion direction prior to use, e.g. during storage or transportation. The distance between the first end of the first support element and the proximal surface of the transcutaneous device may be less than 2 mm, such as less than 1 mm.

The at least one support element may comprise one or more rods or plate structures, each having an end or edge adjacent to or contacting the transcutaneous device for preventing displacement of the transcutaneous device in relation to the carrier part and/or the stationary part in the insertion direction prior to use.

In the initial position of the carrier part, the drive unit may be unbiased

Figure 2:
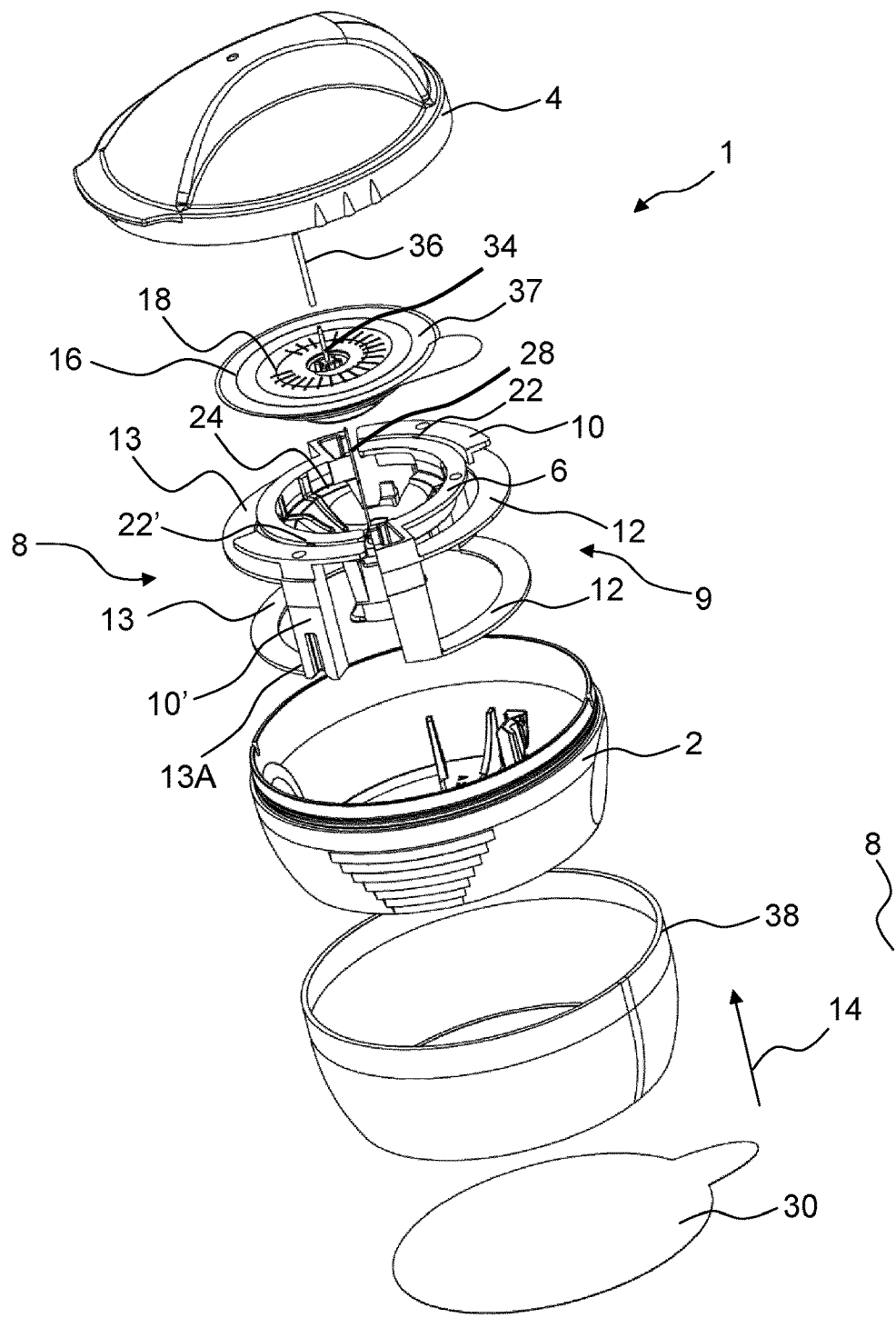
FIG. 2 is a different exploded view of the inserter system in FIG. 1.
Figure 3:
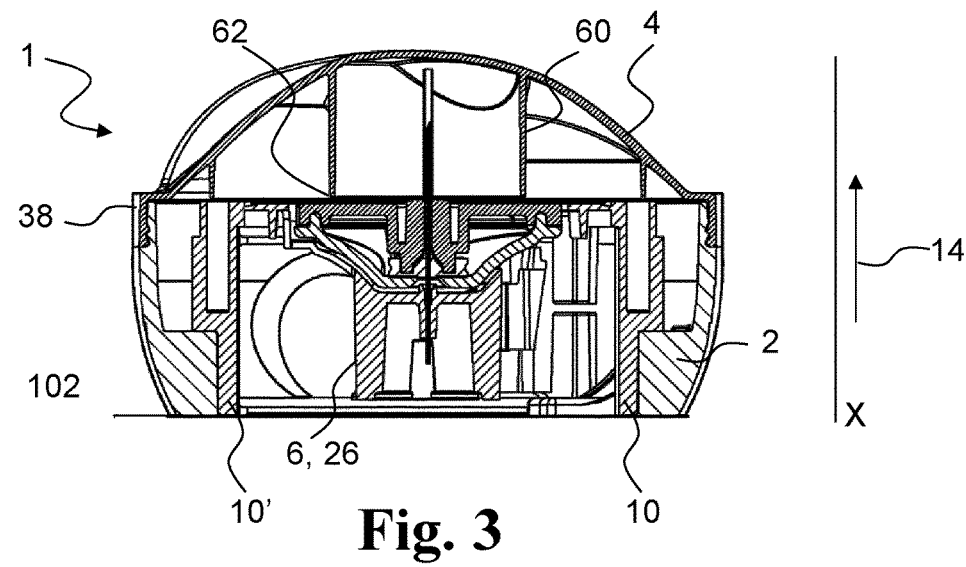
FIG. 3 shows a cross section of the inserter system in FIG. 1.
Figure 4:
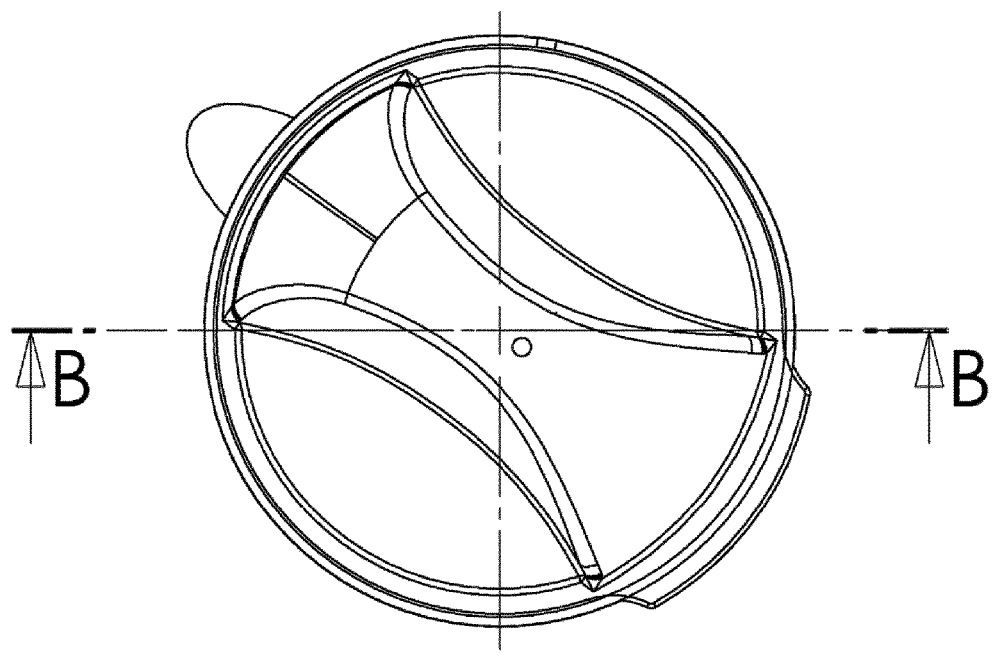
FIG. 4 shows the inserter system of FIG. 1 perpendicular to the insertion direction.

FIGS. 1 and 2 show exploded views of an exemplary inserter system of the present invention and FIG. 3 illustrates a cross section of the inserter system 1 along the line B in FIG. 4. The inserter system 1 comprises a housing part 2 having a sidewall 2' with a first opening 2A at a first end and a second opening 2B at a second end. The inserter system 1 optionally comprises a lid part 4 covering the first opening 2A. Further, the inserter system comprises a carrier part 6 in an initial position in the housing 4 and a drive unit 8 comprising a first drive part attached to the housing. The carrier part 6 and the drive unit 8 form a first unit 9. The carrier part 6 comprises a handle portion 7 for enabling a user to manually load the inserter system by moving the carrier part in the retraction direction opposite the insertion direction 14. The first drive part comprises a first primary drive part 10 and a first secondary drive part 10'. Each first drive part 10, 10' comprises assembly means including an assembly recess 11, 11', respectively, for engaging with corresponding assembly means formed as assembly protrusions in the housing part 2 for mounting the first unit 9 in the housing part 2. The drive unit 8 comprises at least one spring element including two first spring elements in the form of leaf spring elements 12 which at their first ends 12A are connected to the first primary drive part 10 and at their second ends 12B are connected to the carrier part 6. Further, the drive unit 8 comprises two second spring elements in the form of leaf spring elements 13 which at their first ends 13A are connected to the first secondary drive part 10' and at their second ends 13B are connected to the carrier part 6. A configuration with a single spring element such as a helical spring element optionally in combination with guiding means for the carrier part is contemplated. The drive unit 8 is configured for moving the carrier part 6 from a first position to a second position in relation to the housing in an insertion direction 14 along the first axis. The inserter system 1 comprises a transcutaneous device 16 having a base 17 with a proximal surface 18 and a distal surface 20, wherein the transcutaneous device 16 is detachably attached to the carrier part 6 comprising a needle hub 24 including a hub base 26 and optionally an insertion needle 28. The transcutaneous device 16 comprises a transcutaneous element, such as a cannula 34 and/or a sensor element, mounted to the base 17 extending from the proximal surface facing the skin of a patient. The transcutaneous device may comprise a mounting pad 35 secured to the base 17 and having an adhesive proximal surface for securing the transcutaneous device to a base plate and/or on the skin of the patient. A removable protective layer or sheet 37 covers the adhesive surface.

The inserter system 1 comprises at least one transport protection element in the form of a first bridge 22 connecting the first primary drive part 10 and the carrier part 6 in the initial position. Further, the inserter system 1 comprises a second bridge 22' connecting the first secondary drive part 10' and the carrier part 6 in the initial position. A user loading the inserter system breaks the transport protection elements, i.e. bridges 22, 22', when moving the carrier part from the initial position to the first position in relation to the housing. The bridges 22, 22' are molded as a part of the single unit 9 made of POM. The bridges 22, 22' each comprise a weakened section having a minimum width of about 1.0 mm and a minimum thickness of about 0.5 mm for having desired strength to withstand transport shocks and at the same time enabling a user to break the bridges when loading the inserter system.

The housing part 2 comprises a first projecting element 40 and a second projecting element 42 extending from the sidewall 2' and forming a support surface for engagement with locking members 50, 52 of the carrier part 6 for releasably locking the carrier part 6 with the transcutaneous device 16 in the first position.

The at least one transport protection element comprises at least one support element including a first support element 60 formed in the lid part 4 of the inserter system 1. The first support element 60 is formed as a cylindrical tube having a first end 62 and a circular cross section with a first diameter $d_1$, the cylindrical tube extending perpendicular to the first axis. The first support element 60 is arranged to support the transcutaneous device 16 in the initial position by the first end 62 forming a stop member in the insertion direction. The distance between the first end 62 of the first support element 60 and the protective sheet 37 of the transcutaneous device should be small enough, such as less than 2.0 mm, to prevent displacement of the transcutaneous device 16 in relation to the carrier part 6 in the insertion direction prior to use, e.g. during storage or transportation. In one or more embodiments, the first end 62 contacts the protective sheet 37. The at least one support element may comprise one or more rods or plate structures, each having an end or edge adjacent to or contacting the transcutaneous device.

The inserter system 1 optionally comprises a packing film 38 that is shrink-fitted around the housing part and the lid part 4. The packing film 38 is used for showing if the inserter system has been tampered with and therefore may not be sterile.

Figure 5:
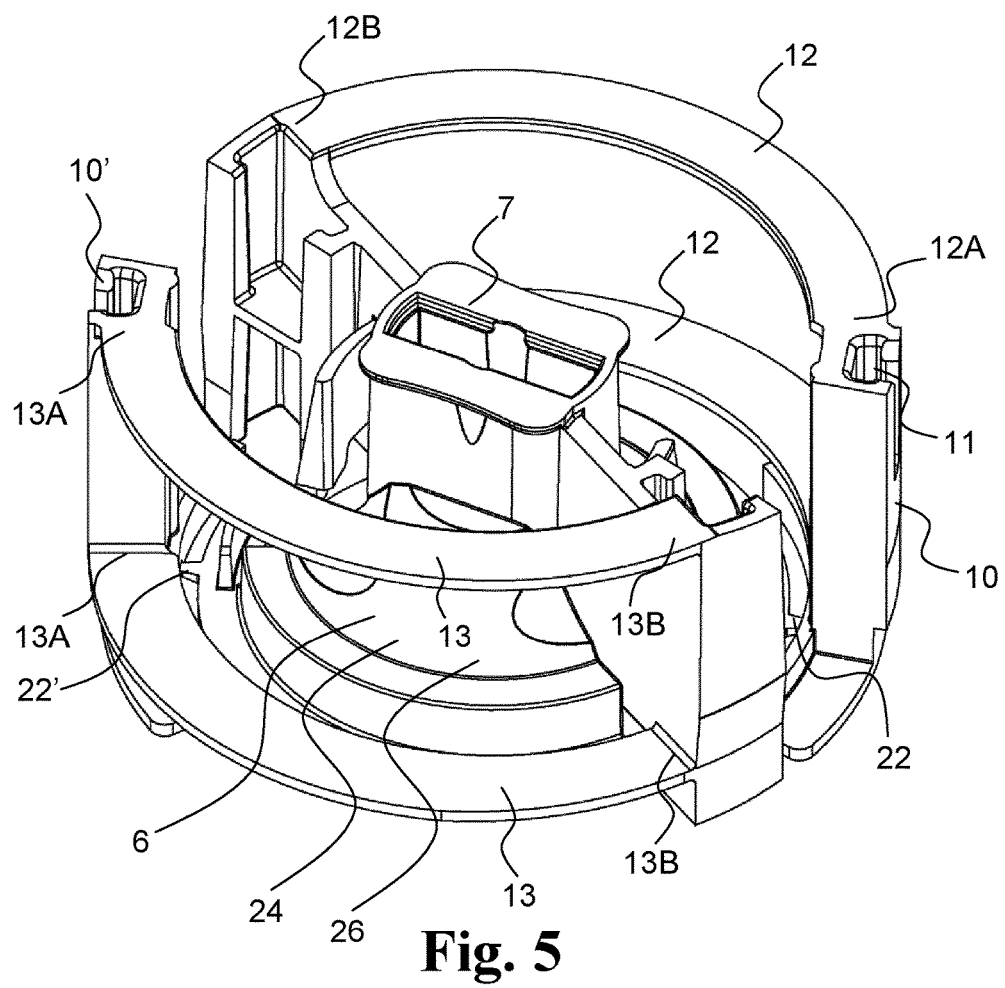
FIG. 5 shows a perspective view of a first unit of an inserter system.
Figure 6:
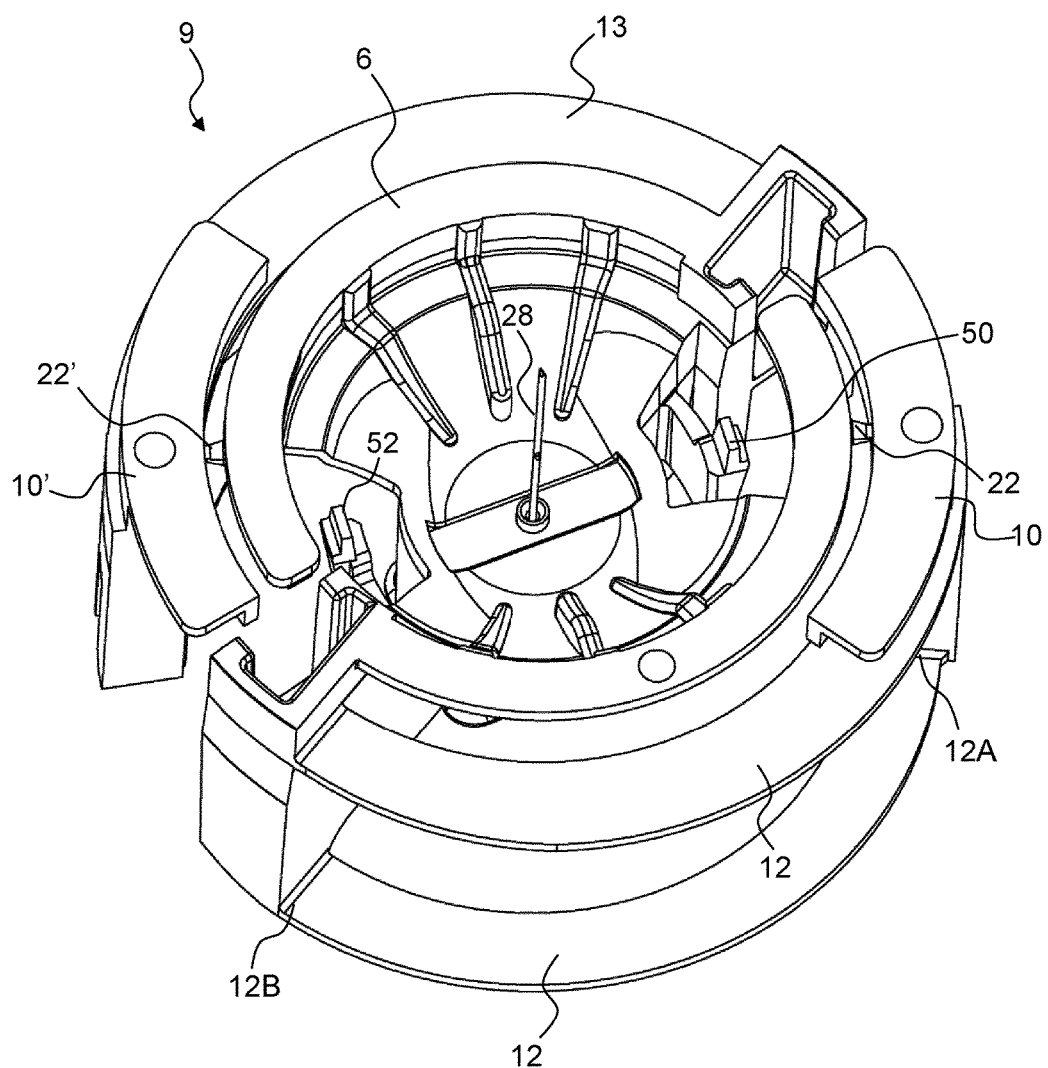
FIG. 6 shows another perspective view of the first unit in FIG. 5.

FIGS. 5 and 6 show different perspective views of the first unit 9 comprising the carrier part 6 and the drive unit 8. The carrier part 6 comprises a first primary locking element 50 and a second locking element 52 for releasably locking the carrier part 6 in the first position by supporting on the projecting elements 40, 42. Alternatively, or in combination, first locking members may be configured to support on first drive part(s) of the drive unit for releasably locking the carrier part in the first position. The locking elements are released by manual deformation of the housing part 2.

Figure 7:
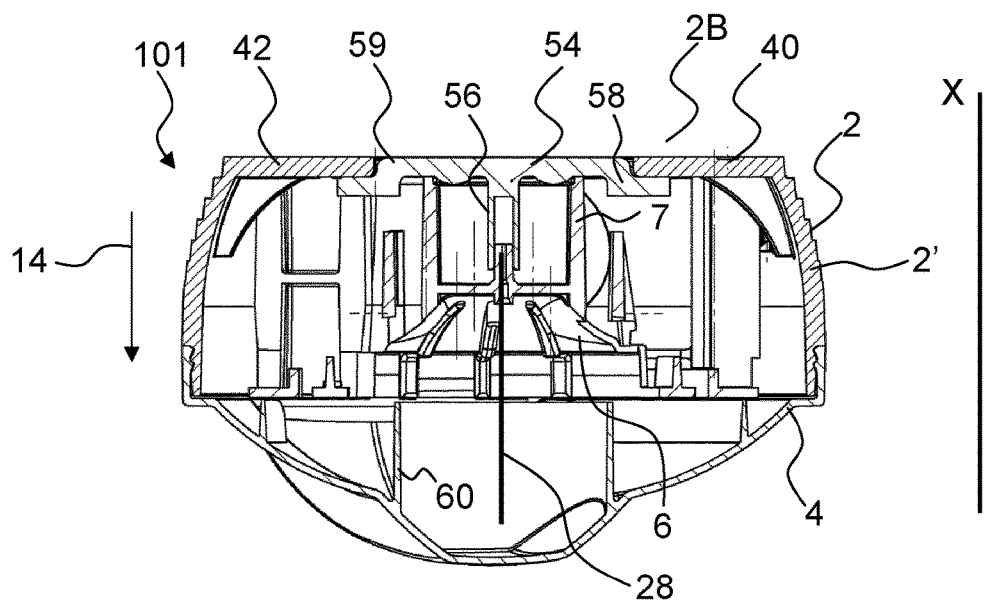
FIG. 7 shows a cross section of an inserter system.
Figure 8:
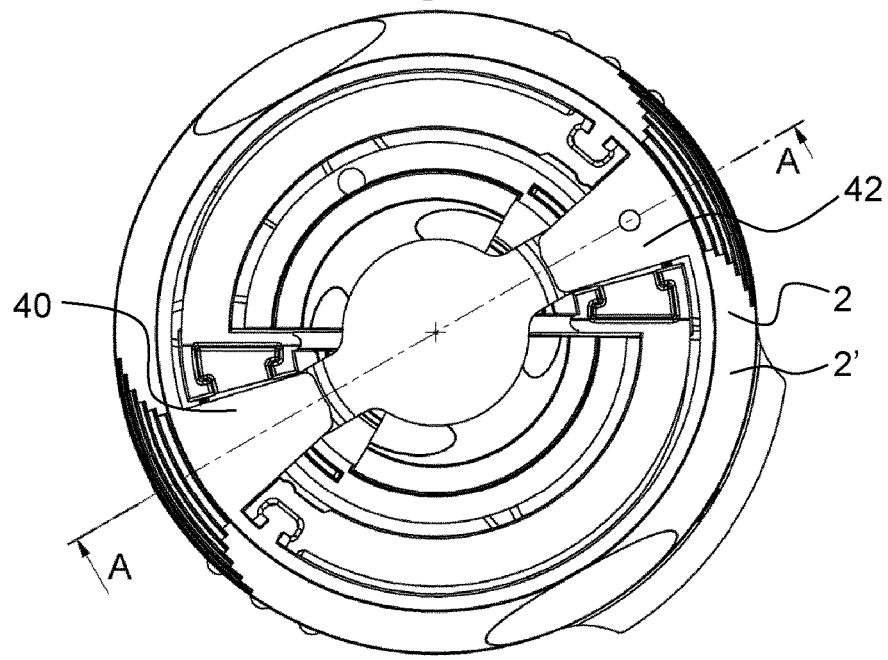
FIG. 8 shows the inserter system of FIG. 7.
Figure 9:
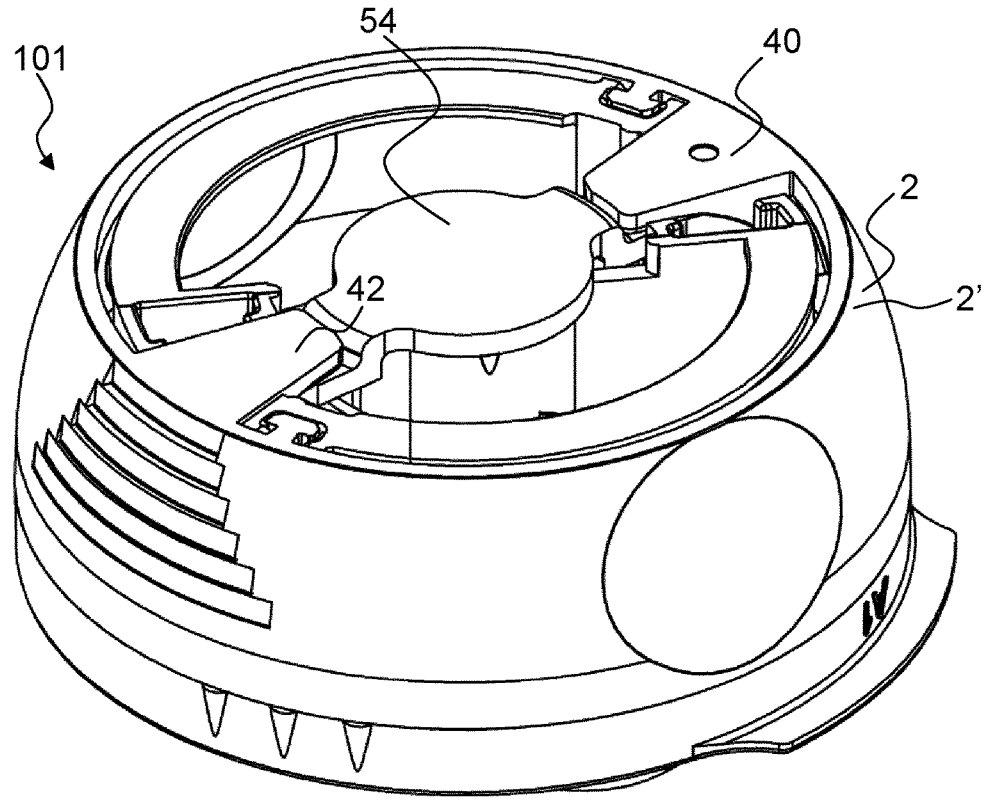
FIG. 9 shows a perspective view of the inserter system in FIG. 7.

FIGS. 7-9 show an inserter system 101 without a transcutaneous device. The inserter system 101 comprises a locking member 54 detachably mounted in the housing part 2. The locking member 54 comprises a first part 56 extending along the first axis X and in the initial position engaging with the handle portion 7 of the carrier part 6. The handle portion 7 forms a cavity, e.g. with rectangular cross section perpendicular to the first axis, for accommodating and supporting the first part 56. Further, the locking member 54 comprises at least one second locking element including a second primary locking element 58 and a second secondary locking element 59 extending perpendicularly to the first axis and supporting on the stationary part (projecting elements 40, 42) of the inserter system 101. Thereby, the carrier part 6 is prevented from moving in the retraction direction in the initial position such that the cover sheet 30 is not damaged by the carrier part moving due to bumps and shocks during transport. In one or more embodiments, the second locking element(s) 58, 59 may be arranged for preventing the carrier part from moving in the insertion direction in the initial position, e.g. by extending into one or more recesses in the stationary part. The locking member 54 may comprise a third locking element (not shown) configured for engaging and locking the carrier part to the locking member 54. The locking member 54 is released by manual rotation, e.g. 90°, of the locking member around the first axis.

Figure 10:
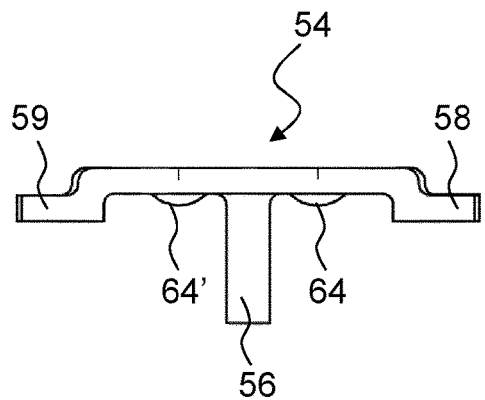
FIG. 10 shows a locking member.

FIG. 10 is a cross sectional view of the locking member 54. The locking member 54 comprises at least one holding element 64, 64' for supporting the locking member in the initial position by extending into the cavity of the handle portion 7 preventing unintentional rotation of the locking member 54 when the inserter system is assembled. When the locking member 54 is rotated by a user, the carrier part 6 is forced slightly in the insertion direction by the holding elements 64, 64'. The locking member 54 is prevented from rotating in the locked initial position, when the lid part 4 with the first support element 60 is assembled with the housing part 2.

LIST OF REFERENCES 1, 101 Inserter system
2 Housing part

2' Sidewall
2A First opening
2B Second opening
4 Lid part
6 Carrier part
7 Handle portion
8 Drive unit
9 First unit
10 First primary drive part
10' First secondary drive part
12 First spring element
12A First end
12B Second end
13 Second spring element
13A First end
13B Second end
14 Insertion direction
16 Trancutaneous device
17 Base
18 Proximal surface
20 Distal surface
22 First bridge
22' Second bridge
24 Needle hub
26 Hub base
28 Insertion needle
30 Seal/cover sheet
34 Cannula
35 Mounting pad
36 Needle protector
37 Protective sheet
38 Packing film
40 First projecting element
42 Second projecting element
50 First primary locking element
52 First secondary locking element
54 Locking member
56 First part
58 Second primary locking element
59 Second secondary locking element
60 First support element
62 First end
64, 64' Holding element
X First axis

The invention claimed is:
1. An inserter system comprising:
a housing part;
a lid part;
a carrier part in an initial position in the housing, wherein the carrier part is movable from the initial position to a retracted position in a direction along or around a first axis;
a drive unit comprising a first drive part attached to the housing, the drive unit comprising at least one spring element supported by the first drive part, wherein the drive unit is configured for moving the carrier part from the retracted position to an insertion position in relation to the housing in an insertion direction along the first axis;
a transcutaneous device having a proximal surface and a distal surface, wherein the transcutaneous device is detachably attached to the carrier part;
at least one transport protection element preventing movement of the carrier part in the direction along or around the first axis thereby supporting the carrier part in the initial position, wherein the at least one transport protection element comprises at least one breakable bridge between the first drive part and the carrier part in the initial position; and
a locking member, wherein the locking member is detachably mounted in the housing part and engaging with the carrier part and a stationary part of the inserter system.

2. The inserter system according to claim 1, wherein the at least one bridge comprises a first bridge between the carrier part and a first primary drive part of the first drive part, and a second bridge between the carrier part and a first secondary drive part of the first drive part.

3. The inserter system according to claim 1, wherein the at least one bridge comprises a first bridge having a minimum width in the range from 0.1 mm to 2.0 mm and a thickness in the range from 0.1 mm to 2.0 mm.

4. The inserter system according to claim 1, wherein the at least one transportation protection element locks the carrier part in the initial position.

5. The inserter system according to claim 4, wherein the at least one transport protection element is configured to release the carrier part prior to movement from the initial position to the retracted position.

6. The inserter system according to claim 1, wherein the at least one spring element is made of a plastic material.

7. The inserter system according to claim 1, wherein the at least one transport protection element comprises at least one support element formed in the lid part, the at least one support element including a first support element for supporting the carrier part and the transcutaneous device in the initial position.

8. The inserter system according to claim 7, wherein the first support element has a first end adjacent to the proximal surface of the transcutaneous device.

9. The inserter system according to claim 1, wherein the carrier part comprises a needle hub with a hub base and an insertion needle secured to the hub base, the transcutaneous device being detachably attached to the needle hub.

10. The inserter system according to claim 9, wherein the carrier part comprises a carrier base releasably attached to the needle hub, wherein the inserter device is configured for releasing the needle hub from the carrier base in the insertion position.

11. The inserter system according to claim 1, wherein the at least one transport protection element comprises a locking member configured for unlocking the carrier part by rotation relative to the carrier part and around the first axis.

12. The inserter system according to claim 1, wherein the at least one breakable bridge breaks at least when the carrier part is moved from the initial position to the retracted position.

13. An inserter system comprising:
a housing part;
a carrier part in an initial position in the housing, wherein the carrier part is movable from the initial position to a retracted position in a direction along or around a first axis;
a drive unit comprising a first drive part attached to the housing, the drive unit comprising at least one biasing element supported by the first drive part, wherein the drive unit is configured for moving the carrier part from the retracted position to an insertion position in relation to the housing in an insertion direction along the first axis;
a transcutaneous device having a proximal surface and a distal surface, wherein the transcutaneous device is detachably attached to the carrier part;

at least one transport protection element preventing movement of the carrier part in the direction along or around the first axis thereby supporting the carrier part in the initial position, wherein the at least one transport protection element comprises at least one breakable bridge between the first drive part and the carrier part in the initial position; and a locking member, wherein the locking member is detachably mounted in the housing part and engaging with the carrier part and a stationary part of the inserter system.

* * * * *